United States Patent
Larkins

(10) Patent No.: US 11,701,325 B2
(45) Date of Patent: Jul. 18, 2023

(54) LIQUID FORMULATION COMPRISING PAEONOL AND APOCYNIN

(71) Applicant: AKL Research & Development Ltd, Manchester (GB)

(72) Inventor: Nicholas John Larkins, London (GB)

(73) Assignee: AKL RESEARCH & DEVELOPMENT LTD, Manchester (GB)

( * ) Notice: Subject to any disclaimer, the term of this patent is extended or adjusted under 35 U.S.C. 154(b) by 0 days.

(21) Appl. No.: 16/765,627

(22) PCT Filed: Nov. 22, 2018

(86) PCT No.: PCT/EP2018/082178
§ 371 (c)(1),
(2) Date: May 20, 2020

(87) PCT Pub. No.: WO2019/101842
PCT Pub. Date: May 31, 2019

(65) Prior Publication Data
US 2020/0297628 A1    Sep. 24, 2020

(30) Foreign Application Priority Data
Nov. 23, 2017 (GB) .................................. 1719464

(51) Int. Cl.
| | |
|---|---|
| *A61P 29/00* | (2006.01) |
| *A61K 9/48* | (2006.01) |
| *A61K 36/539* | (2006.01) |
| *A61K 36/65* | (2006.01) |
| *A61K 9/08* | (2006.01) |
| *A61P 25/28* | (2006.01) |
| *A61K 31/12* | (2006.01) |
| *A61K 47/10* | (2017.01) |
| *A61K 47/14* | (2017.01) |

(52) U.S. Cl.
CPC ............... *A61K 9/08* (2013.01); *A61K 31/12* (2013.01); *A61K 47/10* (2013.01); *A61K 47/14* (2013.01)

(58) Field of Classification Search
CPC .. A61K 2300/00; A61K 31/085; A61K 31/12; A61K 36/24; A61K 36/539; A61K 36/65; A61K 47/10; A61K 47/14; A61K 9/08; A61K 9/48; A61K 9/4858; A61P 25/28; A61P 29/00
USPC ........................................................ 424/400
See application file for complete search history.

(56) References Cited

U.S. PATENT DOCUMENTS

| | | | |
|---|---|---|---|
| 8,841,348 B2 * | 9/2014 | Larkins ................ | A61K 31/216 514/688 |
| 2009/0215886 A1 | 8/2009 | Larkins | |

FOREIGN PATENT DOCUMENTS

| | | | |
|---|---|---|---|
| GB | 2 424 833 A | 10/2006 | |
| GB | 2424833 A * | 10/2006 | ............... A61P 1/04 |
| GB | 2 547 241 A | 8/2017 | |

OTHER PUBLICATIONS

Gullapalli et al.,International Journal of Pharmaceutics 496 (2015) 219-239.*
Gala et al., J Develop Drugs 2013, 2:3.*
Mylius (Justus Liebigs Analen Der Chemie, vol. 587, Published Jan. 7, 1954, pp. 1-15—English language translation appended thereto) (Year: 1954).*
International Search Report corresponding to International Application No. PCT/EP2018/082178, dated Feb. 14, 2019 (4 pages).
Written Opinion of International Searching Authority corresponding to International Application No. PCT/EP2018/082178, dated Feb. 14, 2019 (5 pages).
Wenping Wang et al "Microemulsions based on paeonol-menthol eutectic mixture for enhanced transdermal delivery: formulation development and in vitro evaluation" article in Artificial Cells, Nanomedicine, and Biotechnology, 2017, vol. 45, No. 6, pp. 1241-1246 (6 pages).

* cited by examiner

*Primary Examiner* — Alma Pipic
(74) *Attorney, Agent, or Firm* — Flynn Thiel, P.C.

(57) ABSTRACT

A stable liquid formulation is provided. The liquid formulation includes a composition of active ingredients paeonol and apocynin. Methods of production of such a formation and treatment of diseases administering such a formulation are also provided.

4 Claims, No Drawings

LIQUID FORMULATION COMPRISING PAEONOL AND APOCYNIN

BACKGROUND OF THE INVENTION

The present invention anti-inflammatory and/or analgesic formulations for the treatment of humans or animals. The formulations can also be used in the treatment of neurodegenerative disease.

The combination of active ingredients 4-hydroxy-3-methoxyacetophenone (apocynin) and 2-hydroxy-4-methoxyacetophenone (paeonol) to form a medication for use as an anti-inflammatory is known. One such preparation is known as APPA and has had positive results in the treatment of osteoarthritis in dogs. The APPA formulation combines the active ingredients with a solid excipient. In these solid dose forms such as tablets, heat induced on the tablet during the granulation process and/or on tablet compression can cause transient melting of the low melting point paeonol and subsequent adverse transformation of the physical properties of the active ingredient. Solid phase pharmaceutical preparations also exhibit inferior bioavailability to liquid preparations.

The active ingredients can be brought into the liquid phase by dissolution or suspension in an appropriate liquid and then encapsulated, or in the form of a standardised liquid extract which must be orally ingested by the patient. Such liquid phase preparations possess a reduced concentration of active ingredients. This results in an increase in the number of capsules that need to be taken or increased amount of liquid extract that must be drunk. This is not desirable because the formulation does not taste pleasant and patients prefer not to take large numbers of capsules or drink a large amount of unpleasant tasting medicine. These ease of dose and compliance issues are particularly relevant in clinically vulnerable groups of patients such as those with neurodegenerative diseases.

There is therefore a need for a liquid phase formulation of apocynin and paeonol that possesses a high concentration of active ingredients.

Paeonol is 2-hydroxy-4-methoxyacetophenone and is shown by the following formula:

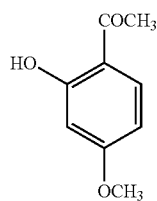

Apocynin is a plant phenol 4-hydroxy-3-methoxyacetophenone, and has the following formula:

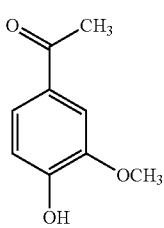

Paeonol is a solid with a low melting point of around 49.7° C. according to our studies. Apocynin is a solid with a much higher melting point of around 114.6° C. according to our studies. APPA is a mixture of paeonol and apocynin, as indicated above.

The compounds are known to be effective in the treatment of inflammatory diseases when mixed at a ratio (by weight) of around 3.5 paeonol:1 apocynin. The applicants have surprisingly found that at (or close to) this ratio a eutectic mixture is formed resulting in a significantly lowered combined melting point of 44.7° C.; below that of both paeonol and apocynin. This is the lowest possible melting point for an APPA system over all mixing ratios.

The applicants have further found that addition of a relatively small quantity of an excipient to the eutectic APPA mixture provides a liquid form of APPA which is stable at room temperature. The excipient may be any suitable oxygenated compound of low toxicity. A number of excipient materials may be suitable including glycols and glycol derivatives, polyhydric alcohols, esters and ethers. Investigation revealed macrogol (polyethylene glycol) 400 to be the most effective. This will be referred to as PEG 400.

When a mixture of 3.5 paeonol:1 apocynin is combined with 2.5 parts of PEG 400 a stable liquid is formed which does not solidify when stored at a temperature of around 3° C.

As only a small quantity of excipient substance is required to induce substantial depression of the melting point, the resulting liquid formulation possesses a relatively high concentration of active compounds. When a mixture of 3.5 paeonol:1 apocynin is combined with 2.5 parts of PEG 400 the stable liquid formed contains 64.3% APPA by weight. Due to the liquid having a high density of 1.1659 g/ml, this equates to 74.5% APPA on a weight per volume basis. Accordingly, the liquid formulation of the invention may provide a highly concentrated form of APPA.

The production of such a highly concentrated liquid formulation made from a eutectic mixture of APPA can be seen as a remarkable discovery allowing for a significant improvement in patient dosing and compliance (amongst other things).

Isomers of apocynin and paeonol are known in the art. Isomers of apocynin and paeonol include 2-hydroxy-3-methoxyacetophenone "orthoacetovanilione" (CAS: 703-98-0), 2-hydroxy-5-methoxyacetophenone (CAS: 705-15-7), 3-hydroxy-4-methoxyacetophenone "isoacetovanilione" (CAS: 6100-74-9) and hydroxy-2-methoxyacetophenone "isopaeonol" (CAS: 493-33-4).

According to the present invention there is provided a liquid formulation comprising active compounds 2-hydroxy-4-methoxyacetophenone (paeonol) or isomer thereof and 4-hydroxy-3-methoxyacetophenone (apocynin) or isomer thereof wherein the ratio by weight of paeonol to apocynin is from 3:2 to 9:1.

According to the present invention there is further provided a liquid formulation comprising active compounds 2-hydroxy-4-methoxyacetophenone (paeonol) or isomer thereof and 4-hydroxy-3-methoxyacetophenone (apocynin) or isomer thereof wherein the ratio by weight of paeonol to apocynin is from 3:2 to 9:1, the formulation further comprising at least one excipient wherein the ratio y weight of total active compounds (i.e the total weight of paeonol and apocynin) to excipient is from 2:3 to 19:1. Preferably, the ratio by weight of total active compounds to excipient is from 2:3 to 9:1.

Preferably the liquid formulation is made from a eutectic mixture of 2-hydroxy-4-methoxyacetophenone (paeonol) or isomer thereof and 4-hydroxy-3-methoxyacetophenone (apocynin) or isomer thereof.

Preferably the liquid formulation comprises active compounds 2-hydroxy-4-methoxyacetophenone (paeonol) and 4-hydroxy-3-methoxyacetophenone (apocynin) wherein the ratio by weight of paeonol to apocynin is from 3:2 to 9:1, the formulation further comprising at least one excipient wherein the ratio by weight of total active compounds (i.e the total weight of paeonol and apocynin) to excipient is from 2:3 to 19:1. Preferably, the ratio by weight of total active compounds to excipient is from 2:3 to 9:1.

Apocynin and paeonol are isomers of each other. It will be appreciated that according to the present invention the liquid formulation comprises two different active compounds (e.g. apocynin itself and paeonol itself).

The excipient may be any suitable oxygenated compound of low toxicity. It will be appreciated that in the context of the present invention the term low toxicity may refer to a material whose toxicity is suitable for long term oral administration along with APPA to humans without adverse effects.

Preferably the excipient is a glycol or glycol derivative, a polyhydric alcohol, or an ester and/or ether thereof. Preferably, the excipient is a glycol. Preferably the excipient is a polyethylene glycol. More preferably the excipient is polyethylene glycol 400. A preferred formulation has a ratio by weight of paeonol or isomer thereof to apocynin or isomer thereof that is from 80:20 to 77.7:22.3. Preferably, the ratio by weight of total active compounds to excipient is 64:36.

Preferably the formulation is a stable liquid at room temperature (15 to 25° C.).

A high concentration of APPA formulation allows for an acceptable dose to be contain within a single soft gel capsule. For example, a 0.533 ml mixture of 3.5 paeonol:1 apocynin with 2.5 parts PEG 400 contains 400 mg of APPA. This is a pharmaceutically effective dose of active compounds of volume small enough to fit into a single soft gel capsule. Further, a 1.07 ml mixture of 3.5 paeonol:1 apocynin with 2.5 parts PEG 400 contains 800 mg of APPA. This is also a pharmaceutically effective dose of active compounds of volume small enough to fit into a single soft gel capsule.

DETAILED DESCRIPTION OF THE PREFERRED EMBODIMENTS

According to the present invention there is provided a liquid formulation made from a eutectic mixture comprising active compounds paeonol or isomer thereof and apocynin or isomer thereof.

According to the present invention there is further provided a liquid formulation made from a eutectic mixture comprising active compounds paeonol or isomer thereof and apocynin or isomer thereof, the liquid formulation further comprising at least one excipient.

Preferably the liquid formulation is made from a eutectic mixture comprising active compounds paeonol and apocynin, the liquid formulation further comprising at least one excipient.

Apocynin and paeonol are isomers of each other. It will be appreciated that according to the present invention the liquid formulation comprises two different active compounds (e.g apocynin itself and paeonol itself).

The excipient may be any suitable oxygenated compound of low toxicity. It will be appreciated that in the context of the present invention the term low toxicity may refer to a material whose toxicity is suitable for long term oral administration along with APPA to humans without adverse effects.

Preferably the excipient is a glycol or glycol derivative, a polyhydric alcohol, or an ester and/or ether thereof. Preferably the excipient is a glycol. Preferably the excipient is a polyethylene glycol. More preferably the excipient is polyethylene glycol 400.

A preferred formulation has a ratio by weight of total active compounds to excipient from 2:3 to 19:1. Preferably, the ratio by weight of total active compounds to excipient is from 2:3 to 9:1. Preferably, the ratio by weight of total active compounds to excipient is 64:36.

Preferably the formulation is a stable liquid at room temperature (15 to 25° C.).

Apocynin is found in plant substances and plant extracts, for example in extracts of the plants picrorrhiza kurroa, apocynum cannabinium, apocynum venatum, apocynum androsaemifolium and *vanilla* species such as *Vanilla planifolia*.

The formulations and preparations of the invention Include 2-hydroxy-4-methoxy-acetophenone (apocynin). Preferably the apocynin has been synthesised, or extracted from plants and purified. This may be referred to as isolated apocynin. The quantities and ratios described herein refer to isolated apocynin.

Apocynin may be present formulations or preparations according to the invention as direct extracts from plants such as those mentioned above (for example as part of an unresolved mixture of compounds in the form of an unpurified plant or root extract). These will be referred to as apocynin "in the natural form" or "natural apocynin". For example, apocynin present in preparations according to the invention in the form of picrorrhiza kurroa will be referred to as "natural apocynin". The term "natural apocynin" or apocynin "in the natural form" also includes glycosides of apocynin such as those found in the plant species in which apocynin is found. Such glycosides include androsin and other iridoid glycoside, for example.

The formulation may include apocynin as part of an unresolved mixture of compounds in the form of an unpurified plant or root extract: "natural" apocynin. Picrorrhiza kurroa is a standardised form based on standardised iridoid glucoside fraction; such forms are well known. A picrorrhiza kurroa in standardised form comprises picrorrhiza kurroa standardised to "Kutkin min 4%". Kutkin is obtained by crystallization and consists of the glucosides picroside I and kutoside in a ratio of 1:2 and other minor glycoside (Sing and Rastogi, 1972, Ansari et al., 1988).

Isolated apocynin provides a more consistent quality of apocynin compared to natural apocynin. It can also be produced on a larger scale to that of natural apocynin. Consequently, isolated apocynin is preferably used in the present invention.

As indicated above, the formulation may include apocynin which is in the natural form, although this is less preferred. If natural apocynin is used the skilled person would readily understand how to adjust the ratios to produce a formulation of the invention. However, if this is the case it may be necessary to limit the amount of picrorrhiza kurroa to prevent side effects (such as stomach upset which may occur due to other phytochemical species in the picrorrhiza kurroa). However, it is noted that most human subjects can take up to 2,000 mg of picrorrhiza kurroa (Kutkin min 2%) per day without discomfort.

Paeonol may be found in plant substances and plant extracts. For example paeonol may be found in Paeonia suffruticosa Paeonia lactiflora, Paeonia veitchii, Paeonia obovata, *Rheum palmatum* (rhizome) and *Scutellaria baicalensis* (root). The formulations and preparations of the invention include 2-hydroxy-4-methoxy-acetophenone (paeonol).

Preferably, paeonol has been synthesised or extracted from plants and purified. This may be referred to as isolated paeonol. The quantities and ratios described herein refer to isolated paeonol. Less preferably, paeonol may be present in preparations according to the invention as direct extracts from plants (i.e. as part of an unresolved mixture of compounds in the form of an unpurified plant or root extract). These will be referred to a paeonol"in the natural form" or"natural paeonol". For example, paeonol present in preparations according to the invention in the form of Paeonia suffruticosa will be referred to as"natural paeonol". The terms paeonol "in the natural form" or"natural paeonol" include glycosides of paeonol such as those found in the plant species in which paeonol is found. Such glycosides include paeonin, paeonolide and paeonoside, for example. If natural paeonol is used the skilled person would readily understand how to adjust the ratios to provide a formulation of the invention.

Isolated paeonol provides a more consistent quality of paeonol compared to natural paeonol. It can also be produced on a larger scale to that of natural paeonol. Consequently, isolated paeonol is preferably used in the present application. The formulations of the present invention may be used in the treatment of inflammatory disease. The formulations of the present invention may also be used in the treatment of neurodegenerative disease.

According to the present invention there is provided a method of production of a liquid formulation comprising active compounds paeonol or isomer thereof and apocynin or isomer thereof comprising (a) forming a eutectic mixture of active compounds paeonol or isomer thereof and apocynin or isomer thereof.

According to the present invention there is further provided a method of production of a liquid formulation comprising active compounds paeonol or isomer thereof and apocynin or isomers thereof comprising (a) forming a eutectic mixture of active compounds paeonol or isomer thereof and apocynin or isomer thereof; and (b) adding an excipient (e.g a glycol).

According to the present invention there is provided a formulation made from a eutectic mixture comprising active compounds paeonol or isomer thereof and apocynin or isomer thereof. Preferably the formulation is a liquid.

The present invention will now be described in detail with reference to the following examples.

EXAMPLE 1

To produce a 1000 mg APPA formulation that is a stable liquid at room temperature, 777.8 mg paeonol is mixed with 222.2 mg apocynin. The mixture is heated and 555.6 mg PEG 400 is added while the mixture is being agitated. A stable mixture is produced which does not solidify when stored at approximately 3° C. overnight.

EXAMPLE 2

400 mg APPA Capsule

To produce a formulation containing approximately 400 mg of APPA, 311.1 mg paeonol is mixed with 88.9 mg apocynin. The mixture is heated and 222.2 mg PEG 400 is added while the mixture is being agitated. This yields a 0.533 ml liquid formulation of paeonol and apocynin which is stable at room temperature. This may be encapsulated within a soft gel capsule by methods known in the art to provide a pharmaceutical product in the form of a capsule.

EXAMPLE 3

800 mg APPA Capsule

To produce a formulation containing approximately 800 mg of APPA, 622.2 mg paeonol is be mixed with 177.8 mg apocynin. The mixture is heated and 444.4 mg PEG 400 is added while the mixture is being agitated. This yields a 1.07 ml liquid formulation of paeonol and apocynin which is stable at room temperature. This may be encapsulated within a soft gel capsule by methods known in the art to provide a pharmaceutical product in the form of a capsule.

The invention claimed is:

1. A method of production of a liquid formulation comprising active compounds paeonol or isomer thereof and apocynin or isomer thereof comprising (a) forming a eutectic mixture of active compounds paeonol or isomer thereof and apocynin or isomer thereof.

2. A method of production according to claim 1 further comprising (b) adding an excipient.

3. A formulation made from a eutectic mixture comprising active compounds paeonol or isomer thereof and apocynin or isomer thereof, wherein the formulation is a liquid.

4. A liquid formulation made from a eutectic mixture comprising active compounds paeonol or isomer thereof and apocynin or isomer thereof, the liquid formulation further comprising at least one excipient.

\* \* \* \* \*